United States Patent [19]

Gold et al.

[11] Patent Number: 5,254,549
[45] Date of Patent: Oct. 19, 1993

[54] NEW BHT ETHER COMPOUNDS AND THEIR USE AS HYPOLIPIDEMIC AND ANTIATHEROSCLEROTIC DRUGS

[75] Inventors: Markus R. Gold, Nauheim; Panayiotis Jarglis; Heinz Junglas, both of Frankfurt; Juergen H. Leimner, Niedernhausen; Dezsoe Peteri, Breunigweiler; Guenter P. Quack, Frankfurt; Josef Strohmeier, Alzenau/Hörstein; Petra M. Wülfroth, Liederbach, all of Fed. Rep. of Germany

[73] Assignee: Merz & Co. GmbH & Co., Frankfurt, Fed. Rep. of Germany

[21] Appl. No.: 810,214

[22] Filed: Dec. 19, 1991

[51] Int. Cl.[5] .................... A01N 43/58; C07D 211/18
[52] U.S. Cl. .................................. 514/247; 514/824; 546/339
[58] Field of Search ................ 546/339; 514/824, 247

[56] References Cited

U.S. PATENT DOCUMENTS 4,745,120  5/1988  Wess et al. ...................... 546/339

FOREIGN PATENT DOCUMENTS 271625  10/1977  Fed. Rep. of Germany ...... 546/339

OTHER PUBLICATIONS

Svedmyr et al., "The relationship between the plasma concentration of free nicotinic acid and some of its pharmacologic effects in man", Clinical Pharmacology and Therapeutics 10, 559–570 (1969).

Primary Examiner—C. Warren Ivy
Assistant Examiner—Raymond Covington
Attorney, Agent, or Firm—Gordon W. Hueschen

[57] ABSTRACT

Pharmaceutically-active BHT-omega pyridyl ethers of the formula selected from BHT-omega-pyridyl ether compounds of the formula:

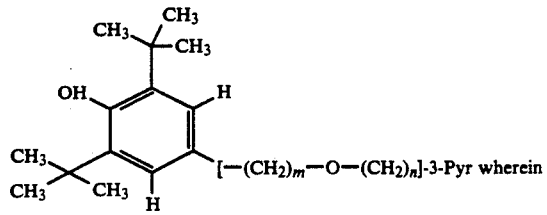

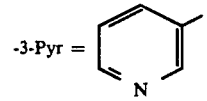

wherein
m = 1,3
for m = 1, Σ = 6–9
for m = 3, Σ = 5–11
Sum (Σ) = [m+n+1 (for oxygen)]

wherein the bond between the two carbon atoms of the $(CH_2)_n$ moiety most closely adjacent the pyridine ring is a single, double, or triple bond, and pharmaceutically-acceptable acid addition salts thereof, pharmaceutical compositions thereof, and a method of combating lipidemia and atherosclerosis therewith, are disclosed.

12 Claims, No Drawings

NEW BHT ETHER COMPOUNDS AND THEIR USE AS HYPOLIPIDEMIC AND ANTIATHEROSCLEROTIC DRUGS

FIELD OF THE INVENTION

Hypolipidemic and antiatherosclerotic compounds, pharmaceutical compositions thereof, and use thereof.

BACKGROUND OF INVENTION AND PRIOR ART

Since the beginning of medical history, atherosclerosis has been described as an important disease. However, only in the twentieth century was it discovered that myocardial infarction is always associated with coronary atherosclerosis and thrombosis. Epidemiologic studies carried out in the seventies have shown that about fifty percent of all mortalities in the Western industrialized countries are caused by cardiovascular disease.

The most important factors in the development of atherosclerosis are known. The importance of elevated cholesterol and triglyceride concentrations was discovered early. Cholesterol and triglycerides are transported in the form of so-called lipoproteins, the cholesterol-rich low-density (LDL) and triglyceride-rich very low-density (VLDL) fractions of which are considered as atherogenic if their concentrations in the blood are increased.

However, only recently was it discovered that in addition to their amount, the "quality" of LDL is also decisive. Thus, in animal experiments it could be shown that equally high concentrations of LDL cholesterol were more or less atherogenic depending upon the properties of the drug applied to redued the elevated LDL cholesterol level. The cause of this finding could also be shown by the authors, namely, a drug which was also able to reduce LDL oxidation was most effective in counteracting atherosclerosis. (Carew et al., Proc. Nat. Acad. Sci. USA 84, 7725-7729 (November 1987.)) This experiment impressively demonstrates the importance of LDL "quality". In the body, LDL and VLDL are subject to continual oxidation which is physiologically balanced by natural so-called antioxidants such as tocopherol or ascorbic acid. However, in the case of increased LDL (cholesterol) and VLDL (triglyceride) values, this homeostasis is disturbed and shifted in favor of an increasing tendency towards oxidation.

Therefore, the risk of development and manifestation of atherosclerosis is increased by two factors:
- elevated concentration of so-called atherogenic lipoproteins (LDL, VLDL) and
- their content of oxidation products (e.g., oxidized lipids).

Causal treatment must, therefore, influence both factors.

Apart from the humoral factors, namely the lipoproteins, the cellular constituents of the vascular wall play an important role in atherogenesis. Thus, in the case of mechanical or chemical damage of the internal vascular coating, the endothelium, a proliferation impulse is generated to stimulate the underlying layer of smooth muscle cells. This process is particularly impressive after endothelial damage as a result of angioplasty. Within a relatively short time the induced proliferate can block the vessel to such an extent that an infarction may occur. In addition to mechanical endothelial damage, noxae such as oxidized LDL play also an important part.

Therefore, in addition to the two possibilities mentioned above, effective atherosclerosis intervention must be aimed at protecting the endothelium and reducing excessive proliferation of smooth muscle cells.

Compounds fulfilling all the above-mentioned requirements should comprise two pharmacologically differently-acting moieties, at least:
- nicotinic acid or a suitable derivative thereof as the lipid-lowering principle.
- an antioxidant as the antiatherosclerosis principle.

Nicotinic acid is the drug of choice as it acts not only on lipids but has been shown to have antiatherosclerolic properties of its own.

Yet, for medication purposes, one must circumvent the known side effects of nicotinic acid, e.g., flush due to a too rapid increase of nicotinic acid concentration in the blood. In fact, it has been found that rapid increases and high levels of nicotinic acid are not necessary to achieve the lipid-lowering effect. Thus, low nicotinic acid concentrations and sufficient reduction of lipids should be the main prerequisites of valuable compounds of the aforementioned type.

DE 2716125 discloses, as a preferred compound, a BHT (butylated hydroxy toluene) ether derivative (herein named Mrz 3/156) of the formula:

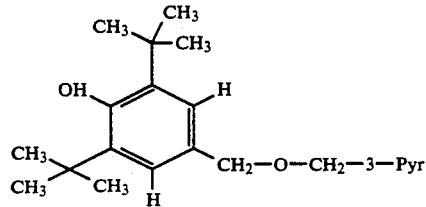

When tested for the required properties, excessively high levels of nicotinic acid (cf. Table 1) were observed, thereby demonstrating that this compound does not fulfill the stated requirements.

Extensive and painstaking synthetic and pharmacological efforts have revealed that there are several structural prerequisites necessary to meet all the criteria.

It was concluded that only compounds of the below-mentioned general formula are of interest.

It could be shown that the compounds according to the invention are
- effective in reducing lipids without induction of excessively high levels of nicotinic acid;
- effective in counteracting lipid and lipoprotein oxidation;
- effective in reducing endothelial damage due to oxidized LDL; and
- effective in reducing the proliferation of smooth muscle cells in the vascular wall.

OBJECTS OF THE INVENTION

It is an object of the invention to provide new and more effective hypolipidemic and antiatherosclerotic compounds, pharmaceutical compositions thereof, and method of treating hyperlipidemia and atherosclerosis therewith. It is a further object of the invention to provide such novel compounds, compositions, and method which fulfill the foregoing theoretical requirements. Additional objects will become apparent hereinafter, and still other objects of the invention will be Apparent to one skilled in the art.

SUMMARY OF THE INVENTION

The invention, then, comprises the following aspects, inter alia, singly or in combination:

a compound selected from those BHT-omega-pyridyl ether compounds of the formula:

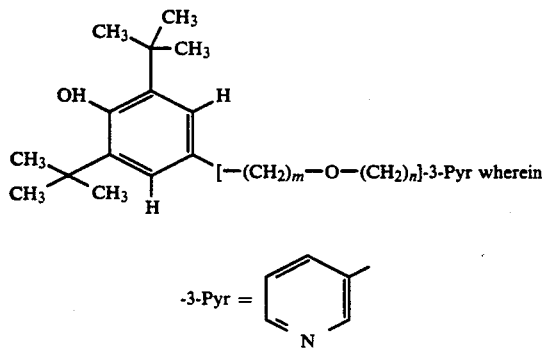

wherein
m = 1,3
for m=1, $\Sigma=6-9$ (n thus being 4-7)
for m=3, $\Sigma=5-11$ (n thus being 1-7)
Sum $(\Sigma)=[m+n+1$ (for oxygen)]
wherein the bond between the two carbon atoms of the $(CH_2)_n$ moiety most closely adjacent the pyridine ring is a single, double, or triple bond, pharmaceutically-acceptable acid addition salts thereof, pharmaceutical compositions useful for combating hyperlipidemia and atherosclerosis comprising such a compound together with a pharmaceutically-acceptable carrier or diluent, and a method of combating hyperlipidemia and atherosclerosis comprising the step of administering to a living animal, i-ncluding a human being, in need thereof, an ef fective antityperlipidemic and antiatherosclerotic amount of such a compound.

GENERAL DESCRIPTION OF THE INVENTION

The present invention relates to ethers of a BHT-derivative (a butylated hydroxy toluene derivative) and an omega-pyridylalkyl-, -alkenyl-, or -alkinyl-alcohol as active hypolipidemic and antiatherosclerotic compound. More particularly, it relates to such an ether compound of the formula:

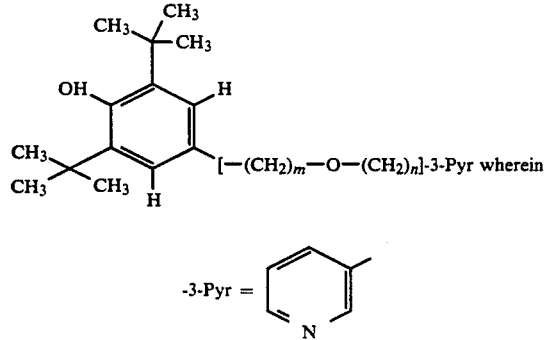

wherein
m = 1, 3
for m=1, $\Sigma=6-9$
for m=3, $\Sigma=5-11$
$\Sigma=[m+n+1$ (for oxygen)]
wherein $(CH_2)_n$ may optionally include a double bond or a triple bond conjugated to the 3-position of the pyridine ring, that is, the bond between the two carbon atoms of the $(CH_2)n$ moiety most closely adjacent the pyridine ring may be a single, double, or triple bond, and a pharmaceutically-acceptable acid addition salt thereof, as well as a pharmaceutical composition containing a compound of the invention as active ingredient, both 6i which are useful as antilipidemic and antiatherosclerotic agents, and a method of combating hyperlipidemia and atherosclerosis therewith.

PHARMACOLOGY a) Kinetics of nicotinic acid

The kinetics of nicotinic acid released from the compounds under investigation was studied in the rat. A single dose (0.2 mmol/kg) of the test substance was administered to fasting normolipidemic rats by gavage. 240 and 360 minutes thereafter, blood samples were taken and the concentration of nicotinic acid in serum was determined using a GC/MS method (n=5 rats per time).

The data are given in table 1.

Table 1: Concentration of nicotinic acid (mg/1) in pooled serum samples after a single application of drug.

| | Nicotinic acid | |
|---|---|---|
| Test compound | Time 240' | Time 360' |
| 3/156 | 4.8 | 5.0 |
| 3/161 | 0.2 | 0.2 |
| 3/187 | 0.58 | 0.23 |
| 3/192 | 0.54 | 0.85 |
| 3/179 | 0.21 | 0.15 |
| 3/188 | 0.17 | 0.18 |
| 3/124 | 0.67 | 0.61 |
| 3/190 | 0.18 | 0.13 |
| 3/191 | 0.47 | 0.44 |
| 3/181 | 0.23 | 0.12 | b) Evidence of lipid-lowering properties

The lipid-lowering properties of the compounds according to the invention were investigated in a rat model. In this model a single dose (0.2 mmol/kg) of the test substance was administered to fasting normolipidemic rats by the oral route. 240 and 360 minutes after application, blood samples were taken, the concentrations of triglycerides being assessed by a standard method (namely GPO-PAP method, E. Merck-system, Darrdstadt, Germany) (n=5 rats per measurement time).

In Table 2 the mean changes are given in percent as compared to a solvent (cremophor, 30% in aqua dest) control.

Table 2: Mean changes ($\Delta$ mean reduction) in percent of triglyceride concentrations 240 and 360 minutes after a single application versus vehicle-treated control.

| | Triglycerides | |
|---|---|---|
| Test Compound | Time 240' | Time 360' |
| 3/161 | 60 | 67 |
| 3/187 | 65 | 55 |
| 3/192 | 44 | 53 |
| 3/179 | 57 | 70 |
| 3/188 | 53 | 40 |
| 3/124 | 73 | 76 |

-continued

| | Triglycerides | |
|---|---|---|
| Test Compound | Time 240' | Time 360' |
| 3/190 | 56 | 28 |
| 3/191 | 37 | 32 |
| 3/181 | 57 | 57 |
| Control | 0 | 0 |

C) Evidence of antioxidant properties

The antioxidant properties of the compounds according to the invention were studied in in-vitro tests. In these tests the substance was incubated with the substrate to be oxidized (synthetic triglyceride with unsaturated fatty acids, i.e., trilinolenine or human LDL). After the incubation period, the degree of oxidation was determined using the so called thiobarbituric acid (TBA) assay. TBA reacts with malondialdehyde (MDA), which is one of the essential oxidation products. The reaction product was assayed photometrically.

c1) Trilinolenine assay

400 μl of trilinolenine was incubated for 3 h at 37° C. with 2 ml HAM F 10 medium with vehicle (namely, ethanol, 0.5% final concentration) or test substance (concentration: $5 \times 10^{-5}$ M) (oxidation is effected without special catalysts).

The total TBA-reactive material was determined in 1 ml of the incubate by adding 1.5 ml of 0.67% TBA solution to 0.05 N NAOH and 1.5 ml to a 20% trichloroacetic acid solution. The mixture was reacted for 60 min. on a boiling water bath. After cooling, absorption was determined at 532 nm.

Three preparations were tested per test compound.

c2) LDL assay

LDL (d=1.019-1.063) was obtained from human plasma by ultracentifugation under addition of EDTA. 100 μg of LDL was incubated with 0.5 ml of HAM F 10 medium for 24 h at 370° C. with vehicle (namely ethanol, 0.5% final concentration) or test substance (concentration: $5 \times 10^{-5}$ M) in the presence of 10 μM of $Cu^{2+}$.

The total TBA-reactive material was determined in accordance with the trilinolenine assay.

Three preparations were tested per test compound.

Tables 3a (trilinolenine assay) and 3b (LDL assay) represent the mean changes in percent as compared to solvent control.

Table 3: mean change (Δ mean reduction) in percent of the concentration of TBA-reactive material after 3-h (a: trilinolenine assay) and 24-h (b: LDL assay) incubation versus vehicle-treated control preparation.

| Test Compound | a) Trilinolenine assay % | b) LDL assay % |
|---|---|---|
| 3/161 | 58 | 79 |
| 3/187 | 71 | 82 |
| 3/192 | 74 | 86 |
| 3/179 | 79 | 73 |
| 3/188 | 66 | 71 |
| 3/124 | 76 | 90 |
| 3/190 | 72 | 89 |
| 3/191 | 76 | 86 |
| 3/181 | 76 | 76 |
| Control | 0 | 0 | d. Evidence of endothelial protection against cytotoxic effects of oxidized LDL

Human endothelial cells of the umbilical vein were isolated after collagenase vascular treatment and cultured.

For the assay the cells were dispersed in a density of 50,000 per dish and cultivated for 4 days with Ham's F 12/DMEM medium (ratio: 4:1) under addition of 15% fetal calf serum, 5% horse serum and 10 ng/ml ECGF heparin.

After 4 days the cells were washed with serum-free medium and used in the cytotox assay.

For this assay the cells were incubated for 24 h at 37° C. in 1 ml of Ham's F 10 medium (+ECGF heparin) with LDL (200 μg/ml). During this time period either the vehicle, namely, ethanol, 0.5% final concentration (control preparation 1) or the test substance ($2 \times 10^{-5}$M) was present. In parallel, one preparation was incubated without LDL and without any other substance and with vehicle (0.5% ethanol) to assess the maximum proliferation rate (control preparation 2).

After 24 h the resultant TBA-reactive material was determined in the medium or the number of cells counted.

Three preparations were tested per test compound.

Table 4a represents the mean changes in percent versus appropriate control preparation 1.

Table 4b shows the number of cells in percent as compared to appropriate control preparation 2.

Table 4a: Mean change (Δ mean reduction) in percent of the concentration of TBA-reactive material after incubation of endothelial cells for 24 h with LDL versus appropriate control preparation 1.

Table 4b: Mean number of cells in percent after 24-h incubation with LDL as compared to appropriate control preparation 2.

| Test | a) TBA-reactive material % | b) Number of endothelial cells % |
|---|---|---|
| 3/187 | 53 | 80 |
| 3/192 | 47 | 79 |
| 3/161 | 64 | 107 |
| 3/181 | 65 | 122 |
| 3/179 | 43 | 76 |
| 3/188 | 54 | 79 |
| 3/124 | 57 | 118 |
| 3/190 | 36 | 65 |
| 3/191 | 33 | 63 |
| Control | 0 | 100 | e. Evidence of the antiproliferative effect on smooth muscle cells in vitro

Smooth muscle cells, obtained after isolation from the aorta of balloon-catheterized rats, were cultivated in DMEM under addition of 10% of fetal calf serum and subject to passages.

For the assay 10,000 cells of one passage were inoculated per dish and incubated for 3 days with vehicle (namely DMSO, 0.5% final concentration) or test compound ($5 \times 10^{-5}$ M) 4 h after innoculation. After 3 days a cell count was made. Six preparations-Were tested per test compound.

Table 5 shows the me n changes in percent versus solvent control.

Table 5: Mean change (Δ mean reduction) in percent of the number of smooth vascular muscle cells after incubation with test substance for 3 days as compared to vehicle-treated control preparation.

| Test compound | Number of cells % |
|---|---|
| 3/161 | 98 |
| 3/187 | 93 |
| 3/192 | 95 |
| 3/179 | 55 |
| 3/188 | 63 |
| 3/124 | 71 |
| 3/190 | 91 |
| 3/191 | 79 |
| 3/181 | 81 |

SYNTHESIS OF THE COMPOUNDS OF THE INVENTION

The preparation of the compounds of the invention is carried out starting from an omega-pyridylalkyl-, alkenyl-, or alkynyl-alcohol, which is reacted with 3,5-ditert.-butyl-4-hydroxy-benzyl alcohol in the form of its acetate:

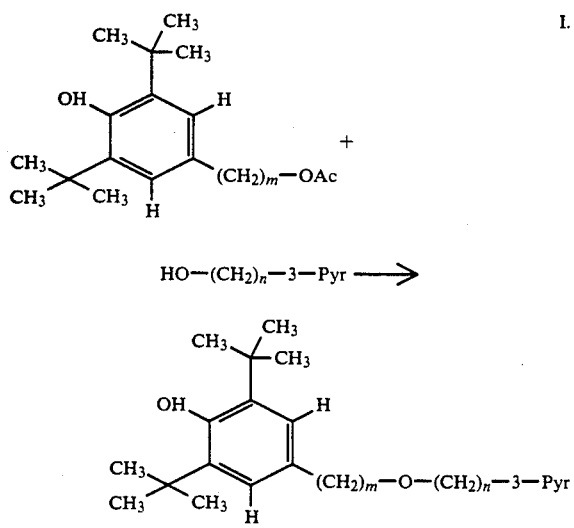

wherein further details and meanings are as previously defined.

The ω-pyridyl-alkyl-alcohol is prepared by a Wittig-reaction starting from pyridyl-3-aldehyde and a phosphonium salt, synthesized from the corresponding halo-alkylalcohol. The resulting unsaturated ω-pyridyl-alkyl-alcohol is directly—or after hydrogenation—converted into a claimed ether.

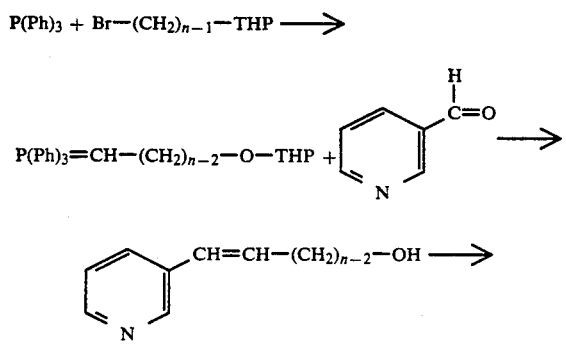

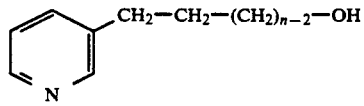

THP = Tetrahydropyranyl

Alternatively, the starting ω-pyridyl-alkyl-alcohol can be prepared by reacting 3-bromopyridine and the corresponding omega-alkynyl alcohol. The resulting ω-pyridylalkynyl-alcohol is converted directly—or after hydrogenation to an ω-pyridyl-alkenyl- or ω-pyridyl-alkyl-alcohol- into a claimed compound of Formula I.

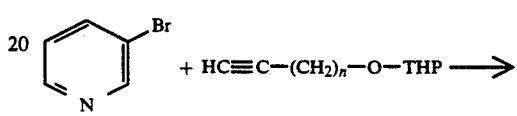

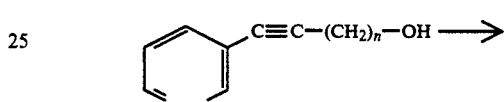

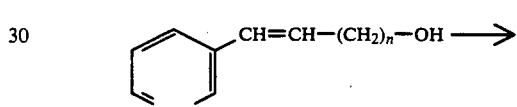

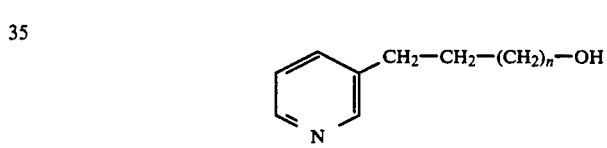

The invention also includes the pharmaceutically-acceptable acid addition salts of the above compounds.

The compounds of Formula I include specifically the following compounds:

1. 2,6-Di-tert-butyl-4-[8-(3-pyridyl)-2-oxaoctyl]phenol (Mrz 3/161)
2. 2,6-Di-tert-butyl-4-[6-(3-pyridyl)-2-oxahexyl]phenol (Mrz 3/187)
3. 2,6-Di-tert-butyl-4-[7-(3-pyridyl)-2-oxaheptyl]phenol (Mrz 3/192)
4. (Z)-2,6-Di-tert-butyl-4-(8-(3-pyridyl)-2-oxaoct-7-enyl]-phenol (Mrz 3/181)
5. 2,6-Di-tert-butyl-4-[9-(3-pyridyl)-2-oxanonyl]phenol (Mrz 3/188)
6. 2,6-Di-tert-butyl-4-(5-(3-pyridyl)-4-oxapentyl]phenol (Mrz 3/124)
7. 2,6-Di-tert-butyl-4-[7-(3-pyridyl)-4-oxaheptyl]phenol (Mrz 3/190)
8. 2,6-Di-tert-butyl-4-[9-(3-pyridyl)-4-oxanonyl)phenol (Mrz 3/191)
9. 2,6-Di-tert-butyl-4-[8-(3-pyridyl)-2-oxaoct-7-ynyl]-phenol (Mrz 3/179), of which 2,6-Di-tert-butyl-4-[8-(3-pyridyl)-2-oxaoctyl]phenol and 2,6-Di-tert-butyl-4-(5-(3-pyridyl)-4-oxapentyl]phenol are preferred.

The following Examples are given to illustrate the preparation of the compounds of the present invention, but are not to be construed as limiting.

EXAMPLE 1

Synthesis of 2, 6-Di-tert-butyl-4- ( 8- (3-pyridyl)-2-oxaoctyl]phenol

STEP 1

3,5-Di-tert-butyl-4-hydroxybenzylacetate 102.1 g (1 mol) of acetic anhydride is slowly added to a stirred solution of 118 g (0.5 mol) of 3,5-di-tert-butyl-4-hydroxybenzylalcohol in 90 ml pyridine at 0° C. After 15 minutes, the cooling-bath is removed and the solution reacted an additional two hours at ambient temperature. Then, the reaction mixture is poured under vigorous stirring into ice-water. After 15 minutes the precipitated product is collected by filtration, washed with water, dried and recrystallized from hexanes, yielding 110 g (80%) of 3,5-di-tert-butyl-4-hydroxybenzylacetate as a yellowish cystalline solid, m.p. 108° C. ($C_{17}H_{26}O_3$; Formula Weight (F.W.) 278.2).

Rf: 0.57 ($SiO_2$ 60; n-hexane/diethyl ether 3:1).

STEP 2

6-(3-Pyridyl)hexanol

A solution of 45 ml (0.47 mol) of 3-bromopyridine and 52 g (0.53 mol) of 5-hexyn-1-ol in 150 ml of triethylamine and 500 ml of dichloromethane is degassed for 15 minutes with argon, and 3 g (4.3 mmol) of bis(triphenylphosphine)palladium(II)chloride and -350 mg of cuprous iodide is added. The mixture is heated at reflux for 3 h. The cooled reaction mixture is diluted with 1 liter of dichloromethane and is washed with water and brine, dried ($K_2CO_3$), concentrated and bulb-to-bulb distilled (b.p. 120°-130° C./0.05 mbar), to give 63 g of 6-(3-pyridyl)hex-5-ynol as a yellow oil, which is dissolved in 300 ml of isopropanol and hydrogenated for 16 h over 6 g 10% palladium on carbon in a Parr-hydrogenator. The crude product is evaporatively distilled (b.p. 120-130° C./0.05 mbar), yielding 61.8 g (65%) of 6-(3-pyridyl)hexanol as a faintly yellow, viscous liquid. ($C_{11}H_{17}NO$; F.W. 179.3)

STEP 3

2,6-Di-tert-butyl-4-[8-(3-pyridyl)-2-oxaoctyl]phenol

A solution of 1.53 g (5.5 mmol) of 3,5-di-tert-buty-1-4-hydroxybenzylacetate, 895 mg (5 mmol) of 6-(3-pyridy-1)hexanol and 30 mg of tetrakis(triphenylphosphine) palladium(O) in 60 ml of degassed, dry acetonitrile is stirred at room-temperature under a nitrogen-atmosphere for 5 days. The solvent is evaporated, the residue partitioned between ether and saturated aqueous bicarbonate, and the dried extract separated by column-chromatography on silica gel after concentration. The yield of 2,6-di-tert-butyl-4-[8-(3-pyridyl)-2-oxaoctyl]phenol amounts to 59% yellowish viscous oil, slowly crystallizing, m.p. 63° C. ($C_{26}H_{39}NO_2$; F.W. 397.6).

Rf: 0.6 ($SiO_2$ 60; n-hexane/ethyl acetate 3:1 ).

EXAMPLE 2

Synthesis of 2,6-Di-tert-butyl-4-[6-(3-pyridyl)-2-oxahexyl]phenol

STEP 1

2,(3-Bromopropyloxy) tetrahydropyran

To a solution of 35 g (0.251 mol) of 3-bromopropanol and 1 g of p-toluenesulphonic acid in 500 ml of diethylether, 32.5 ml (0.357 mol) of 3,4-dihydro-2H-pyran is added dropwise under cooling with ice water and the solution is stirred for 2 hours at room temperature. The mixture is neutralized with saturated aqueous bicarbonate. washed with brine and concentrated after drying, affording 56 g of 2-(3-bromopropyloxy)tetrahydropyran in practically quantitative yield as a viscous liquid, which may be used without further purification. ($C_8H_{15}BrO_2$; F.W. 223.1).

Rf: 0.9 ($SiO_2$ 60; n-hexane/ethyl acetate 1:1).

STEP 2

3-(Tetrahydropyranyloxy)propyl-triphenylphosphoniuffbromide 66.5 g (0.298 mol) of 2-(3-bromopropyloxy)tetrahydropyran is refluxed together with 82 g (0.312 mol) of triphenylphosphine and 1 g of tetrabutylammonium iodide in 500 ml of acetonitrile for 24 hours. After evaporation of the solvent, the residue is triturated several times with boiling diethylether. 144 g (100%) of 3-(tetrahydropyranyloxy)propyl-triphenylphosphonium bromide is obtained as heavy oil. ($C_{26}H_{30}BrNO_2P$; F.W. 485.4).

STEP 3

2-[4-(3-Pyridyl)but-3-enoxy]tetrahydropyran

To a solution of 33.6 ml (0.24 mol) of diisopropylamine in 300 ml of dry tetrahydrofuran, 149 ml (0.244 mol; 15% solution in hexanes) of butyllithium is added dropwise under an atmosphere of nitrogen at 780C. After stirring for an additional 15 minutes, 115 g (0.237 mol) of 3-(tetrahydropyranyloxy)propyl-triphenylphosphonium bromide, dissolved in 400 ml of dry tetrahydrofuran, is added slowly to the mixture, followed after 30 minutes by a solution of 19 ml (0.199 mol) of freshly-distilled pyridine-3-aldehyde. The reaction mixture is then stirred for 3 hours at −78° C. followed by reaction at ambient temperature for an additional 16 hours. After usual work-up, 87 g (79%) of 2-(4-(3-pyridyl)but-3-enoxyltetrahydropyran is isolated as viscous liquid by chromatographic separation of the crude product mixture. ($C_{14}H_{19}NO_2$; F.W. 233.3).

Rf: 0.2 ($SiO_2$ 60; n-hexane/diethyl ether 1:1).

STEP 4

4-(3-Pyridyl)butanol 10 g (43 mmol) of 2-[4-(3-pyridyl)but-3-enoxy]tetrahydropyran in 200 ml of methanol/water 1:1 (v/v) is acidified by 2N hydrochloric acid and hydrogenated for 16 hours over 2 g 10% palladium on carbon. After filtration, the solvent is removed, the remaining residue is neutralized by saturated aqueous bicarbonate, and the product is extraced with several portions of ether. Purification of the crude product by column chromatography on silica gel yields 15.7 g (87%) of 4-(3-pyridyl)but-Anol as colourless viscous oil. ($C_9H_{13}NO$; F.W. 151.2).

Rf: 0.2 ($SiO_260$; n-hexane/ethyl acetate 1:1).

STEP 5

2,6-Di-tert-butyl-4-[6-(3-pyridyl)-2-oxahexyl]phenol according to EXAMPLE 1 STEP 3

2,6-di-tert-butyl-4-[6-(3-pyridyl)-2-oxahexyl)phenol is obtained as an amber oil in 62% yield for the final etherification step. ($C_{24}H_{35}NO_2$; F.W. 369.6).

Rf: 0.42 ($SiO_2$ 60; n-hexane/ethyl acetate 3:2).

EXAMPLE 3

Synthesisof 2,6-Di-tert-butyl-4-(7-(3-pyridyl)-2-oxaheptyl]phenol according to EXAMPLE 1, STEP 2 (starting from 4-pentyn-1-ol; E.R.H. Jones et al., Org. Synthesis Coll. Vol. 4, 755 (1963)) to STEP 3, 2,6-di-tert-butyl-4-[7-(3-pyridyl)-2-oxaheptyl)phenol is obtained as a heavy yellow syrup in 59% yield in the final etherification step. ($C_{25}H_{37}NO_2$; F.W. 383.6).

Rf: 0.49 ($SiO_2$ 60; n-hexane/ethyl acetate 3:2).

EXAMPLE 4

Synthesis of
(Z)-2,6-Di-tert-butly-4-(8-(3-pyridyl)-2-oxaoct-7-enyl]-phenol

STEP 1

(Z)-6-(3-Pyridyl)hex-5-enol

A solution of 45 ml (0.47 mol) of 3-bromopyridine and 52 g (0.53 mol) of 5-hexyn-l-ol in 150 ml of triethylamine and 500 ml of dichloromethane is degassed for 15 minutes with argon, and 3 g (4,3 mmol) of bis(triphenylphosphine)palladium(II)chloride and 450 mg of cuprous iodide is added. The mixture is heated at reflux for 3 h. The cooled reaction mixture is diluted with 1 liter of dichloromethane and is washed with water and brine, dried ($K_2CO_3$), concentrated and bulb-to-bulb distilled (b.p. 120°–130° C./0.05 mbar), to give 63 g of 6-(3-pyridyl)hex-5-ynol as a yellow oil, which is dissolved in 500 ml of ethyl acetate and af ter addition of 15 ml of quinoline is hydrogenated f or 5 h over 6 g Lindlar catalyst (Pb-poisoned Pd catalyst) in a Parrhydrogenator. The crude product is evaporatively distilled (b.p. 120°–130° C./0.05 mbar), yielding 61 g (73%) of (Z)-6-(3-pyridyl)hex-5-enol as a colourless viscous liquid. ($C_{11}H_{15}NO$; F.W. 177.3).

Rf: 0.21 ($SiO_2$ 60; $CH_2Cl_2$/MeOH 97:3).

STEP 2

(Z)-2,6-Di-tert-butyl-4-[8-(3-pyridyl)-2-oxaoct-7-enyl]phenol according to EXAMPLE 1 STEP 3, using (Z)-6-(3-pyridyl)hex-5-enol as the alcohol component in the etherification reaction. The yield of (Z)-2,6-di-tert-butyl-4-[8-(3-pyridyl)-2-oxaoct-7-enyl]phenol amounts to 49%; yellowish viscous oil, slowly crystallizing, m. p. 44° C. ($C_{26}H_{39}NO_2$; F.W. 397.6).

Rf: 0.4 ($SiO_2$ 60; n-hexane/ethyl acetate 2:1).

EXAMPLE 5

Synthesis of
2,6-Di-tert-butyl-4-[9-(3-pyridyl)-2-oxanonyl]phenol

The starting material 7-(3.pyridyl)heptanol was prepared via a Wittig-route from 6-bromohexanol and nicotine aldehyde, analogous to EXAMPLE 2, STEP 1 to STEP 4. Etherification like in EXAMPLE 1, STEP 3 afforded 2,6-ditert-butyl-4-[9-(3-pyridyl)-2-oxanonyl]-phenol (434); amber coloured viscous liquid. ($C_{27}H_{41}NO_2$; F.W. 411.6).

Rf: 0.48 ($SiO_2$ 60; h-hexane-7cthyl acetate 3:2).

EXAMPLE 6

Synthesis of
2,6-Di-tert-butyl-4-[5-(3-pyridyl)-4-oxapentyl]phenol

STEP 1

3-(3,5-Di-tert-butyl-4-hydroxyphenyl)propanol

A solution of 57.76 g (0.2 mol; 70% soln. in toluene) of sodium bis(2-methoxyethoxy)aluminium hydride in 100 ml of dry toluene is prepared in a 1 liter three-necked flask fitted with a mechanical stirrer, a condenser equipped with a nitrogen inlet, and a 500-ml. pressure-equalizing dropping funnel. The mixture is stirred under cooling with an ice-bath and maintained under a nitrogen atmosphere while a solution of 29.24 g (0.1 mol) of methyl 3-(3,5-di-tert-butyl-4-hydroxyphenyl)propionate (Ionox 520; Shell Chemie GmbH) in 300 ml of anhydrous toluene is added slowly over 30 minutes. Stirring is continued after addition for a 30-minute period at ambient temperature followed by 80 minutes at reflux. The cooled reaction mixture, which has deposited a viscous glassy precipitate in the course of the reaction, is carefully quenched with 1 liter of 3M hydrochloric acid. After usual work-up, the oily crude product is evaporatively bulb-to-bulb distilled at 145°–150° C. (1 Torr) providing 25.7 g (97%) 3-(3,5-di-tert-butyl-4-hydroxyphenyl)propanol as a colourless solid, m.p. 69°–70° C. after recrystallization from n-hexane. ($C_{17}H_{28}O_2$; F.W. 264,4).

Rf: 0.49 ($SiO_2$ 60; Tol/i-PrOH 9:1).

STEP 2

3-(3,5-Di-tert-butyl-4-hydroxyphenyl)-1-(tetrahydropyran-2-yloxy)propane

An ice-cold, stirred solution of 31.06 g (0.117 mol) of 3-(3,5-di-tert-buytl-4-hydroxyphenyl)propanol and 500 mg of pyridinium p-toluenesulphonate (PPTS) in 120 ml of anhydrous dichloromethane is treated over a 15-minute period dropwise with 11.91 g (0.142 mol) of 3,4-dihydro -2H-pyran and, after further 60 minutes in the cooling-bath, is reacted at room temperature overnight. The reaction mixture is washed with saturated aqueous bicarbonate and brine, dried over $Na_2SO_4$ and concentrated in vacuo, leaving 40.74 g (pract. 100%) 3-(3,5-di-tert-butyl-4-hydroxyphenyl)-1-(tetrahydropyran-2yloxy)propane as a yellow oil, which is used without further purification. ($C_{22}H_{36}O_3$; F.W. 348.5).

Rf: 0.57 ($SiO_260$; Tol/i-PrOH 9:1).

STEP 3

3-(4-Acetoxy-3,5-di-tert-butylphenyl)-1-(tetrahydropyran-2-yloxy)propane

A vigourously stirred mixture of 40.74 g (0.117 mol) of 3-(3,5-di-tert-butyl-4-hydroxyphenyl)-1-(tetrahydropyran-2-yloxy)propane and 5.85 g (16.7 mmol) of tetrabutylammonium hydrogen sulphate in 250 ml of dichloromethane and 250 ml of 50% aqueous sodium hydroxide is treated at 0° C. dropwise with 14.32 g (0.140 mol) of acetic anhydride, dissolved in 100 ml of dichloromethane, under a nitrogen atmosphere. After addition is complete, the mixture is reacted for an additional 4-–hour period at ambient temperature. Following usual extradtive work-up, 42.69 g (93%) of 3-(4-acetoxy-3,5-di-tert-butylphenyl)-1-(tetrahydropyran-2-yloxy)propane is obtained as a brown viscous liquid, which is used for the following deprotection step without further purification. ($C_{24}H_{38}O_4$; F.W. 390.6).

Rf: 0.52 ($SiO_2$ 60; Tol/i-PrOH 9:1).

STEP 4

3-(4-Acetoxy-3,5-di-tert.-butylphenyl)-propanol

A solution of 14.6 g (37.38 mmol) of 3-(4-acetoxy-3,5-di-tert-butylphenyl)-1-(tetrahydropyran-2-yloxy)propane in 80 ml of anhydrous methanol is stirred together with 1 g of amberlyst 15 (H+-form) for 2 hours at 45° C. and maintained at room temperature overnight. After dilution of the suspension with 100 ml of methanol, the catalyst is removed by filtration and the filtrate evaporated at reduced pressure leaving 11.53 g of crude product, which is purified by flashchromatography over silica gel with H/AcOEt 3:1 as the eluent. 6.96 g (61%) of 3-(4-acetoxy-3,5-di-tert-butylphenyl)propanol is isolated from the product-containing fractions as a faintly yellowish oil, which gradually crystallizes upon standing, m.p. 93°–95° C. ($C_{19}H_{30}O_3$; F. W. 306.4).

Rf: 0.47 ($SiO_2$ 60; Tol/i-PrOH 9:1).

STEP 5

2,6-Di-tert-butyl-4-[5-(3-pyridyl)-4-oxapentyl]phenol

A solution of 19.74 g (64.42 mmol) of 3-(4-acetoxy -3,5-di-tert-butylphenyl)propanol, 12.68 g (77.3 mmol)

of 3-picolylchloride hydrochloride and 5 g of tetrabutylammonium hydrogen sulphate in 250 ml of toluene is treated with 250 ml of 50% aqueous sodium hydroxide with vigorous stirring (>400 rpm) under a nitrogen atmosphere and external cooling with a watdrbath. Stirring of the dark reaction mixture is continued for an additional 5 hours at room temperature. After usual extractive work-up, the crude product (26.3 g) is purified by flash-chromatography over silica gel with AcOEt/H 2:1 as the eluent, yielding 16.9 g (66%) of 2,6-di-tert-butyl-4-[5-(3-pyridyl)-4-oxapentyl]phenyl acetate as a colourless oil, which is dissolved in 100 ml of dry tetrahydrofuran and added dropwise at −78° C. (acetone/dry ice) under inert conditions to a stirred suspension of 1.77 g (46.76 mmol) lithium aluminium hydride in 100 ml of anhydrous tetrahydrofuran. The reaction mixture is stirred overnight in the gradually-warming cooling bath, maintained for 2 hours at 40OC, and quenched under vigorous stirring and external cooling with ice-water by sequential, careful addition of 1.77 g of water, 1.77 g of 15% aqueous sodium hydroxide and a f inal portaionn of 5.31 g of water. After 1 hour, the resulting suspension is diluted with 200 ml of THF, dried with 20 g of $Na_2SO_4$ and the aluminate precipitate is removed by filtration through a fritted glass funnel and the solvent evaporated at reduced pressure, to give 12.9 g of crude 2,6-di-tert-buty -1-4-[5-(3-pyridyl)-4-oxapentyl)phenol as a yellow solid, leaving 11.49 g (76% for the deprotection step) of pure product, m.p. 105*C, after recrystallization with n-hexane/ethyl acetate. ($C_{23}H_{33}NO_2$; F.W. 355.5).

Rf: 0.37 ($SiO_2$ 60; Tol/i-PrOH 9:1).

EXAMPLE 7

Synthesis of
2,6-Di-tert-butyl-4-[7-(3-pyridyl)-4-oxaheptyl]phenol

STEP 1

3-(4-Acetoxy-3,5-di-tert-butylphenyl)-1-(tosyloxy)-propane

To 8.41 g (27.44 mmol) of 3-(4-acetoxy-3,5-di-tert-butylphenyl)-propanol (see EXAMPLE 6, STEP 3 to STEP 4), dissolved in 125 ml of anhydrous pyridine, is added 5.49 g (28.80 mmol) of p-toluenesulphonyl chloride at 0° C. The reaction mixture is stirred for 1.5 hours at this temperature and stored overnight in the refrigerator and worked up extractively in the usual way. The crude 3-(4-acetoxy -3,5-di-tert-butylphenyl)-1-(tosyloxy)propane is purified by flash-chromatography over silica gel with n-hexan/AcOEt 4:1 as the eluent, affording 8.28 g (664) of pure tosylate as a colourless viscous liquid. ($C_{26}H_{36}SO_5$; F.W. 460.6).

Rf: 0.42 ($SiO_2$60; Tol/i-PrOH 9:1).

STEP 2

2,6-Di-tert-butyl-4-(7-(3-pyridyl)-4-oxaheptyl]phenol

A solution of 3.66 g (26.68 mmol) of 3-(3-pyridyl)-propanol in 30 ml anhydrous THF and 3.5 ml dry HMPA is added via syringe to a stirred suspension of 2.56 g (60% oil dispersion, 53.33 mmol) of NaH in 35 ml of anhydrous THF under an inert atmosphere at 0° C., followed by a 2 h period at reflux. The sodium alcoholate solution is then recooled to 0° C. and 10.68 g (23.19 mmol) of 3-(4-acetoxy-3,5-di-tert-butylphenyl)-1-(tosyloxy)propane, dissolved in 35 ml of anhydrous THF, is added, fo-Wowed by refluxing for 2 h and stirring overnight at room temperature. After usual workup, the crude product (9.88 g; brown oil) is purified by flash-chromatography over silica gel, eluting with n-hexane/ethyl acetate 3:1, yielding 2.88 g (62% of 2,6-ditert-butyl-4-[7-(3-pyridyl)-4-oxaheptyl]phenol as amber oil. ($C_{25}H_{37}NO_2$; F.W. 383.6).

Rf: 0.44 ($SiO_2$ 60; n-hexane/ethyl acetate 3:2).

EXAMPLE 8

Synthesis of
2,6-Di-tert-butyl-4-[9-(3-pyridyl)-4-oxanonyl]phenol 2,6-Di-tert-butyl-4-(9-(3-pyridyl)-4-oxanonyl]phenol Starting with 5-(3-pyridyl)pentanol (preparation: see EXAMPLE 1, step 2, starting with 4-pentyn-1-ol (E. R. H. Jones et al., Org. Synthesis Coll. 4, 755 (1963)), etherification as described above (see EXAMPLE 7), afforded 2,6-di-tert-butyl-4-(9-(3-pyridyl)-4-oxanonyl]phenolin 57% yield as yellowish viscous oil. ($C_{27}H_{41}NO_2$; F.W. 411.6).

Rf: 0.52 ($SiO_2$ 60; n-hexane/ethyl acetate 3:2).

EXAMPLE 9

Synthesis of
2,6-di-tert.-butyl-4-(8-(3-pyridyl)-2-oxaoct-7-ynyl]-phenol

According to EXAMPLE 1 Step 2 (without hydrogenation step) to Step 3, 2,6-di-tert-butyl-4-(8-(3-pyridyl)-2-oxaoct-7-ynyl]phenol is obtained as yellow viscous oil in 62% yield in the final step. ($C_{26}H_{35}NO_2$; F.W. 393.6).

Rf: 0.48 ($SiO_2$60; n-hexane/ethyl acetate 2:1).

ACID ADDITION SALTS

As acids suitable for the formation of acid addition salts according to conventional procedure, there may be mentioned from the mineral Swies the following acids: hydrochloric, hydrobromic, -methanesulfonic, isothionic, sulfuric, phosphoric, and sulfamic acids and, from the organic series: acetic, propionic, maleic, fumaric, tartaric, citric, oxalic, and benzoic acids, to name a few. Preferred acids are hydrochloric, citric, and maleic. Other pharmaceutically-acceptable acid addition salts may be prepared, if desired, and one acid addition salt may be converted into another by neutralizing one salt, for example, the hydrochloride, and reacidifying with a different selected mineral or organic acid, to prepare another pharmaceutically-acceptable acid addition salt, as already explained in the foregoing and as is conventional in the art.

PHARMACEUTICAL COMPOSITIONS

The compounds according to the present invention may be processed into pharmaceutical compositions comprising a pharmaceutically-acceptable carrier or diluent in addition to the active compound of the present invention. Such compositions can be administered to a living animal, especially a living human, by the oral or the parenteral route. For example, solid preparations or pharmaceutical compositions for oral administration may take the form of capsules, tablets, pills, powders, or granulates. In such solid pharmaceutical formulations, the active substance or a prodrug therefor is mixed with at least one pharmaceutically-acceptable diluent or carrier such as cane sugar, lactose, starch, talc, or synthetic or natural gums, a binder such as gelatin, a lubricant such as sodium sterate, and/or a disintegrant such as sodium bicarbonate. To enable a sustained-release effect, a substance such as a hydrocolloid or other polymer may be incorporated into the pharmaceutical composition. Additional substances such as lubricants or buffers may also be added, as is conventional in the art. The tablets, pills, or granulates may be subjected to enteric coating, if desired. Liquids for oral application may be in the form of liposomes, emulsions, solutions, or suspensions, containing commonly-used inert diluents such as water. Additionally, such liquid pharmaceutical compositions may also contain wetting, emulsifying, dispersing, or generally surface-active agents as well as sweetening, flavoring, or fragrance-imparting substances.

Suitable preparations for parenteral application may be, among others, sterile aqueous or non-aqueous solutions, suspensions, liposomes, or emulsions. Additional substances, of which there are many, already known for this form of presentation of a pharmaceutical composition, may be employed as pharmaceutically-acceptable diluent or carrier material.

Depending upon the intended mode of application and duration of treatment, the exact dosage of the active compounds in the preparations of the invention may be varied, especially as deemed appropriate by the attending physician or veterinarian. The active agents of the present invention may obviously be combined for administration with other pharmacologically-active agents.

In the compositions of the present invention, the proportions of the active agent or agents in the composition may be varied widely, it being necessary only that the active ingredient of the invention or a prodrug therefor constitute or provide an effective amount, i.e., such that a suitable effective dose will be obtained consistent with the dosage form employed. Obviously several dosage forms as well as several individual tive compounds may be administered at or about the same-time or even in the same pharmaceutical composition or formulation.

METHOD-OF-TREATING

As previously indicated, the compounds of the present invention are suitable, especially in the form of pharmaceutical compositions or formulations thereof, for oral or parenteral administration, the exact individual dosages as well as daily dosages in a particular case of course being determined according to well-established medical and/or veterinarian principles in accord with the directions of the physician or veterinarian in charge.

In addition to oral and parenteral administration, rectal and/or intravenous administration may be employed, the dosages generally being considerably reduced where parenteral administration is involved, although oral administration is preferred. An amount of approximately one to three grams per day in the form of repeated dosages is suitable. Broader ranges of about 0.5 to about 10 grams per day may also be employed, depending upon the circumstances of an individual case. Although 500 mg of active principle has been found especially suitable for use in tablets, individual dosages may vary from about 200 to 1,000 mg, and the 500 mg suggested for use in tablets may of course be administered orally, for example, from one to three times a day. It goes without saying that more:than one tablet may be administered in a single dose, as would be required to attain the above-identified suggested daily oral administration amounts of one to three grams per day.

As already stated, a compound of the invention or a prodrug therefor may be administered to the living animal including a living human in any one of numerous ways, for example, orally as in capsu ei or tablets, parenterally in the form of sterile solutions or suspensions, or by pellet implantation, and in some cases intravenously in the form of sterile solutions. Other obvious modes of administration are cutaneously, subcutaneously, bucally, intramuscularly, and intraperitoneally, and the particular mode of administration will as usual be selected by the physician or veterinarian in charge.

It is thus seen that the present invention provides novel antilipidemic and antiatherosclerotic BHT-omega pyridyl ether compounds and pharmaceutical compositions thereof, as well as a method of combating hyperlipidemia and atherosclerosis therewith, these collectively providing a long-awaited solution to a previously-existing problem not adequately solved by the prior art.

It is to be understood that the present invention is not to be limited to the exact compounds, compositions, methods, or procedures disclosed, as numerous modifications and changes therein will immediately become apparent to one skilled in the art to which this invention pertains, wherefore the present invention is to be understood as limited only by the full scope which can be legally accorded to the appended claims.

We claim:

1. A compound selected from BHT-omega-pyridyl ether compounds of the formula:

$$\text{structure with OH-substituted phenyl ring bearing two } C(CH_3)_3 \text{ groups and } [-(CH_2)_m-O-(CH_2)_n]\text{-3-Pyr wherein}$$

$$\text{-3-Pyr} = \text{pyridin-3-yl}$$

wherein
$m = 1, 3$
for $m = 1$, $\Sigma = 6-9$ (n thus being 4-7)
for $m = 3$, $\Sigma = 5-11$ (n thus being 1-7)
Sum $(\Sigma) = [m + n + 1$ (for oxygen)]
wherein the bond between the two carbon atoms of the $(CH_2)_n$ moiety most closely adjacent the pyridine ring is a single, double, or triple bond, a-n-d pharmaceutically-acceptable acid addition salts thereof.

2. A compound of claim 1 selected f rom the group consisting of:
2,6-Di-tert-butyl-4-(8-(3-pyridyl)-2-oxaoctyl]phenol,
2,6-Di-tert-butyl-4-[6-(3-pyridyl)-2-oxahexyl]phenol,
2,6-Di-tert-butyl-4-(7-(3-pyridyl)-2-oxaheptyl]phenol,
(Z)-2,6-Di-tert-butyl-4-[8-(3-pyridyl)-2-oxaoct-7-enyl]-phenol,
2,6-Di-tert-butyl-4-[9-(3-pyridyl)-2-oxanonyl]phenol,
2,6-Di-tert-butyl-4-[5-(3-pyridyl)-4-oxapentyl]phenol,
2,6-Di-tert-butyl-4-[7-(3-pyridyl)-4-oxaheptyl]phenol,
2,6-Di-tert-butyl-4-[9-(3-pyridyl)-4-oxanonyl)phenol, and
2, 6-Di-tert-butyl-4- ( 8-(3-pyridyl) -2-oxaoct-7-ynyll phenol.

3. A compound of claim 1 which is 2,6-Di-tert-butyl-4-[8-(3-pyridyl)-2-oxaoctyl]phenol.

4. A compound of claim 1 which is 2,6-Di-tert-butyl-4-[5-(3-pyridyl)-4-oxapentyl]phenol.

5. An antilipidemic and antiatherosclerotic pharmaceutical composition containing as active ingredient an effective antilipidemic and antisclerotic amount of a compound, selected from BHT-omega-pyridyl ether compounds of the formula:

[Structure: phenol ring with OH, two C(CH$_3$)$_3$ groups, and [—(CH$_2$)$_m$—O—(CH$_2$)$_n$]-3-Pyr substituent]

-3-Pyr = [pyridine ring structure]

wherein
m = 1,3
for m=1, Σ=6-9 (n thus being 4-7)
for m=3, Σ=5-11 (n thus being 1-7)
Sum (Σ)=[m+n+1 (for oxygen)]
wherein the bond between the two carbon atoms of the (CH$_2$)$_n$ moiety most closely adjacent the pyridine ring is a single, double, or triple bond,, and pharmaceutically-acceptable acid addition salts thereof, together with a pharmaceutically-acceptable carrier or excipient.

6. A pharmaceutical composition of claim 5 wherein the active ingredient is selected from the group consisting of:

2,6-Di-tert-butyl-4-[8-(3-pyridyl)-2-oxaoctyl]phenol,
2,6-Di-tert-butyl-4-[6-(3-pyridyl)-2-oxahexyl]phenol,
2,6-Di-tert-butyl-4-(7-(3-p-yridyl)-2-oxaheptyl]phenol,
(Z)-2,6-Di-tert-butyl-4-[B-(3-pyridyl)-2-oxaoct-7-enyl]-phenol,
2,6-Di-tert-butyl-4-[9-(3-pyridyl)-2-oxanonyl]phenol,
2,6-Di-tert-butyl-4-[5-(3-pyridyl)-4-oxapentyl]phenol,
2,6-Di-tert-butyl-4-[7-(3-pyridyl)-4-oxaheptyl]phenol,
2,6-Di-tert-butyl-4-[9-(3-pyridyl)-4-oxanonyl)phenol, and
2,6-Di-tert-butyl-4-[8-(3-pyridyl)-2-oxaoct-7-ynyl]-phenol.

7. A pharmaceutical composition of claim 5 wherein the active ingredient is 2,6-Di-tert-butyl-4- 8-(3-pyridyl)-2-oxaoctyl]phenol.

8. A pharmaceutical composition of claim 5 wherein the active ingredient is 2,6-Di-tert-butyl-4-(5-(3-pyridyl)-4-oxapentyl]phenol.

9. A method of combating lipidemia and atherosclerosis in a living animal comprising the step of administering to a living animal in need thereof, an effective antilipidemic and antiatherosclerotic amount of a compound selected from BHT-omega-pyridyl ether compounds of the formula:

[Structure: phenol ring with OH, two C(CH$_3$)$_3$ groups, and [—(CH$_2$)$_m$—O—(CH$_2$)$_n$]-3-Pyr substituent]

-3-Pyr = [pyridine ring structure]

wherein
m = 1, 3
for m=1, Σ=6-9 (n thus being 4-7)
for m=3, Σ=5-11 (n thus being 1-7)
Sum (Σ)=[m+n+1 (for oxygen)]
wherein the bond between the two carbon atoms of the (CH$_2$)$_n$ moiety most closely adjacent the pyridine ring is a single, double, or triple bond, and pharmaceutically-acceptable acid addition salts thereof, or a pharmaceutical composition thereof.

10. A method of claim 9 wherein the compound is selected from the group consisting of:
2,6-Di-tert-butyl-4-[8-(3-pyridyl)-2-oxaoctyl]phenol,
2,6-Di-tert-butyl-4-[6-(3-pyridyl)-2-oxahexyl]phenol,
2,6-Di-tert-butyl-4-(7-(3-pyridyl)-2-oxaheptyl]phenol,
(Z)-2,6-Di-tert-butyl-4-[8-(3-pyridyl)-2-oxaoct-7-enyl]-phenol,
2,6-Di-tert-butyl-4-[9-(3-pyridyl)-2-oxanonyl]phenol,
2,6-Di-tert-butyl-4-[5-(3-pyridyl)-4-oxapentyl]phenol,
2,6-Di-tert-butyl-4-[7-(3-pyridyl)-4-oxaheptyl]phenol,
2,6-Di-tert-butyl-4-(9-(3-pyridyl)-4-oxanonyl)phenol, and
2,6-Di-tert-butyl-4-[8-(3 - fidyl)-2-oxaoct-7-ynyl]-phenol.

11. A method of claim 10, wherein the active ingredient is 2,6-Di-tert-butyl-4-[A-(3-pyridyl)-2-oxaoctyl]phenol.

12. A method of claim 10, wherein the active ingredient is 2,6-Di-tert-butyl-4-[5-(3-pyridyl)-4-oxapentyl]phenol.

* * * * *

UNITED STATES PATENT AND TRADEMARK OFFICE
CERTIFICATE OF CORRECTION

PATENT NO. : 5,254,549

DATED : October 19, 1993

Page 1 of 4

INVENTOR(S) : Markus R. Gold, Panayiotis Jarglis, Heinz Junglas, Juergen H. Leimner, Dezsoe Peteri, Guenter P. Quack, Josef Strohmeier, and Petra M. Wülfroth It is certified that error appears in the above-indentified patent and that said Letters Patent is hereby corrected as shown below:

Col. 1, line 36; "redued" should read -- reduce --.
Col. 3, line 1; "Apparent" should read -- apparent --.
Col. 3, line 39; "i-ncluding" should read -- including -- and delete "ef" at the end of the line.
Col. 3, line 40; "fective" should read -- effective -- and "antiftyperlipidemic" should read -- antihyperlipidemic --.
Col. 4, line 10; replace "6i" with -- of --.
Col. 5, line 31; "NAOH" should read -- NaOH --.
Col. 5, line 40; "370°" should read -- 37° --.
Col. 5, line 43; "Cu²+" should read -- $Cu^{2+}$ --.
Col. 5, line 50; "Table 3: mean" should read -- Table 3: Mean --.
Col. 6, line 13; delete the space between "f" and "or".
Col. 6, line 61; "preparations-Were" should read -- preparations were --.
Col. 6, line 63; "me n" should read -- mean --.
Col. 8, line 43; delete the space between "specif" and "ically".
Col. 8, line 51; replace the parenthesis "(" between "4-" and "8-" by a bracket -- [ --.
Col. 8, line 55; replace the parenthesis "(" between "4-" and "5-" by a bracket -- [ --.
Col. 8, line 65; replace the parenthesis "(" between "4-" and "5-" by a bracket -- [ --.
Col. 9, line 3; replace the parenthesis "(" between "4-" and "8-" by a bracket -- [ --.
Col. 9, line 13; delete the space between "Af" and "ter".
Col. 9, line 26; "-350" should read -- 450 --.
Col. 9, line 43; "pyridy-1" should read -- pyridyl-1 --.
Col. 9, line 67; replace the period after "ate" with a comma.
Col. 10, line 7; "phoniuffbromide" should read -- phoniumbromide --.

UNITED STATES PATENT AND TRADEMARK OFFICE
CERTIFICATE OF CORRECTION

PATENT NO. : 5,254,549

DATED : October 19, 1993

Page 2 of 4

INVENTOR(S) : Markus R. Gold, Panayiotis Jarglis, Heinz Junglas, Juergen H. Leimner, Dezsoe Peteri, Guenter P. Quack, Josef Strohmeier, and Petra M. Wülfroth It is certified that error appears in the above-indentified patent and that said Letters Patent is hereby corrected as shown below:

Col. 10, line 23; "780C." should read -- 78°C. --.
Col. 10, line 33; replace the parenthesis "(" between "2-" and "4-" with a bracket -- [ --.
Col. 10, line 34; "enoxyltetrahydropyran" should read -- enoxy]tetrahydropyran --.
Col. 10, line 49; "Anol" should read -- anol --.
Col. 10, line 61; insert a space between "Synthesis" and "of" and replace the parenthesis "(" between "4-" and " 7 - " with a bracket -- [ --.
Col. 11, line 4; replace the parenthesis "(" between "4-" and "8-" with a bracket -- [ --.
Col. 11, line 19; delete the space between "af" and "ter".
Col. 11, line 20; delete the space between "f" and "or".
Col. 11, line 42; "(3.pyridyl)" should read -- (3-pyridyl) --.
Col. 11, line 46; insert a hyphen between "di" and "tert".
Col. 11, line 47; "(434);" should read -- (43%); --.
Col. 11, line 49; "h-hexane-7cthyl" should read -- n-hexane/ethyl --.
Col. 12, line 9; "264,4" should read -- 264.4 --.
Col. 12, line 25; insert a hyphen between "2" and "yloxy".
Col. 12, line 41; "4--hour" should read -- 4-hour --.
Col. 12, line 49; delete the period after "tert".
Col. 13, line 5; "watdr-" should read -- water- --.
Col. 13, line 18; "400C" should read -- 40°C --
Col. 13, line 22; "f inal portaionn" should read -- final portion --.
Col. 13, line 27; "buty" should read -- butyl --.
Col. 13, line 30; "105*C" should read -- 105°C --.
Col. 13, line 50; "(664)" should read -- (66%) --.
Col. 13, line 65; "fo-Wowed" should read -- followed --.
Col. 14, line 2; insert a hyphen betwee "di" and "tert".

UNITED STATES PATENT AND TRADEMARK OFFICE
CERTIFICATE OF CORRECTION

PATENT NO. : 5,254,549

DATED : October 19, 1993

INVENTOR(S) : Markus R. Gold, Panayiotis Jarglis, Heinz Junglas, Juergen H. Leimner, Dezsoe Peteri, Guenter P. Quack, Josef Strohmeier, and Petra M. Wülfroth It is certified that error appears in the above-indentified patent and that said Letters Patent is hereby corrected as shown below:

Col. 14, line 10; replace the parenthesis "(" between "4-" and "9-" with a bracket -- [ --.
Col. 14, line 15; replace the parenthesis "(" between "4-" and "9-" with a bracket -- [ --.
Col. 14, line 16; insert a space between "phenol" and "in".
Col. 14, line 23; delete the period after "tert" and replace the parenthesis "(" between "4-" and "8-" with a bracket -- [ --.
Col. 14, line 26; replace the parenthesis "(" between "4-" and "8-" with a bracket -- [ --.
Col. 14, line 35; "Swies" should read -- series --.
Col. 14, line 36; delete the hyphen before "methanesulfonic".
Col. 15, line 34; "tive" should read -- active --.
Col. 15, line 35; delete the hyphen between "same" and "time".
Col. 15, line 63; "more:than" should read -- more than --.
Col. 16, line 2; "capsu ei" should read -- capsules --.
Col. 16, line 53; "a-n-d" should read -- and --.
Col. 16, line 55; delete the space between "f" and "rom".
Col. 16, line 57; replace the parenthesis "(" between "4-" and "8-" with a bracket -- [ --.
Col. 16, line 59; replace the parenthesis "(" between "4-" and "7-" with a bracket -- [ --.
Col. 16, line 65; replace the parenthesis ")" between "oxa-nonyl" and "phenol," with a bracket -- ] --.
Col. 16, line 67; delete the space between "2," and "6", replace the parenthesis "(" between "4-" and "8-" with a bracket -- [ -- and "ynyll" should read -- ynyl]- --.
Col. 17, line 43; replace the parenthesis "(" between "4-" and "7-" with a bracket -- [ -- and delete the hyphen between "p" and "yridyl".
Col. 17, line 54; insert a -- [ -- between "4-" and "8-".

UNITED STATES PATENT AND TRADEMARK OFFICE
CERTIFICATE OF CORRECTION

PATENT NO. : 5,254,549

DATED : October 19, 1993

INVENTOR(S) : Markus R. Gold, Panayiotis Jarglis, Heinz Junglas, Juergen H. Leimner, Dezsoe Peteri, Guenter P. Quack, Josef Strohmeier, and Petra M. Wülfroth It is certified that error appears in the above-indentified patent and that said Letters Patent is hereby corrected as shown below:

Col. 17, line 44; "B" should read -- 8 --.
Col. 17, line 54; insert a bracket -- [ -- between "4-" and "8-(3-".
Col. 18, line 2; replace the parenthesis "(" between "4-" and "5-" with a bracket -- [ --.
Col. 18, line 39; replace the parenthesis "(" between "4-" and "7-" with a bracket -- [ --.
Col. 18, line 45; replace the parenthesis "(" between "4-" and "9-" with a bracket -- [ --.
Col. 18, line 47; "(3 - fidyl)" should read -- (3-pyridyl) --
Col. 18, line 51; "[A" should read -- [8 --.

Signed and Sealed this

Twenty-sixth Day of July, 1994

Attest:

BRUCE LEHMAN

Attesting Officer     Commissioner of Patents and Trademarks